(12) United States Patent
Sanford et al.

(10) Patent No.: US 6,182,507 B1
(45) Date of Patent: Feb. 6, 2001

(54) MECHANICAL WATER SENSOR

(75) Inventors: Matthew J. Sanford, Bel Alton, MD (US); Keith B. Lewis, King George, VA (US)

(73) Assignee: The United States of America as represented by the Secretary of the Navy, Washington, DC (US)

(*) Notice: Under 35 U.S.C. 154(b), the term of this patent shall be extended for 0 days.

(21) Appl. No.: 09/206,940

(22) Filed: Dec. 8, 1998

(51) Int. Cl.[7] .................................................. G01N 19/10
(52) U.S. Cl. ............................................................. 73/335.06
(58) Field of Search .............................. 73/29.02, 29.01, 73/335.07, 61.43, 335.03, 335.04, 335.06; 136/242; 324/685, 689; 401/52

(56) References Cited

U.S. PATENT DOCUMENTS

| | | | |
|---|---|---|---|
| 2,977,798 | 4/1961 | Dean ........................................ | 73/335 |
| 3,857,284 | 12/1974 | Carron et al. ......................... | 73/336.5 |
| 4,793,180 | 12/1988 | Stewart et al. .......................... | 73/335 |

*Primary Examiner*—William Oen
(74) *Attorney, Agent, or Firm*—James B. Bechtel, Esq.; Peter J. Van Bergen, Esq.

(57) ABSTRACT

A water sensor includes a housing that has at least one inlet port formed therein for allowing water to pass therethrough when submerged in water. A drive piston is mounted in the housing for sliding engagement therein. A water-activated driver is coupled to the drive piston and is in communication with the inlet port(s). The water-activated driver is inert in air and reactive with water to exert pressure on the drive piston and so that the drive piston moves in the housing. A movable indicator is mounted relative to the housing and is positioned to be responsive to movement of the drive piston. The movable indicator moves from a first position to a second position in response to movement of the drive piston.

20 Claims, 3 Drawing Sheets

US 6,182,507 B1

MECHANICAL WATER SENSOR

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to water sensing devices, and more particularly to a sensor that positively detects the presence of water in a mechanical fashion.

BACKGROUND OF THE INVENTION

Water sensors are well known in the art. One conventional design approach uses water pressure to indicate the presence of water since water pressure increases rapidly with depth. However, such sensors are ineffective in shallow water (i.e., less than five feet) where the difference between the water pressure and ambient air pressure is very small. Another conventional design approach is to sense the presence of water in an electronic fashion. However, these sensors require a power source which must be checked/replaced periodically, generally have more potential failure modes, require extensive testing using fault tree analysis, and may not be robust enough to withstand harsh environmental conditions.

SUMMARY OF THE INVENTION

Accordingly, it is an object of the present invention to provide a water sensor.

Another object of the present invention is to provide a water sensor that positively detects the presence of water in a shallow water environment.

Still an other object of the present invention is to provide a water sensor that detects the presence of water in a simple mechanical fashion.

Other objects and advantages of the present invention will become more obvious hereinafter in the specification and drawings.

In accordance with the present invention, a water sensor includes a housing that has at least one inlet port formed therein for allowing water to pass therethrough when submerged in water. A drive piston is mounted in the housing for sliding engagement therein. A water-activated driver is coupled to the drive piston and is in communication with the inlet port(s). The water-activated driver is inert in air and reactive with water to exert pressure on the drive piston and so that the drive piston moves in the housing. A movable indicator is mounted relative to the housing and is positioned to be responsive to movement of the drive piston. The movable indicator moves from a first position to a second position in response to movement of the drive piston.

DETAILED DESCRIPTION OF THE INVENTION

The present invention is a simple mechanical water sensor that positively indicates the presence of water even when the sensor is submerged in shallow water depths. The water sensor cannot be activated in air and is therefore well-suited to be incorporated into the safety system of an underwater explosive device to prevent premature (i.e., "in air") activation thereof.

It is to be understood at the outset that the novel features of the present invention could be realized in a variety of specific embodiments. By way of example, two such embodiments will be described herein. Various features of the two embodiments are interchangeable as will be noted below.

Figure 1:
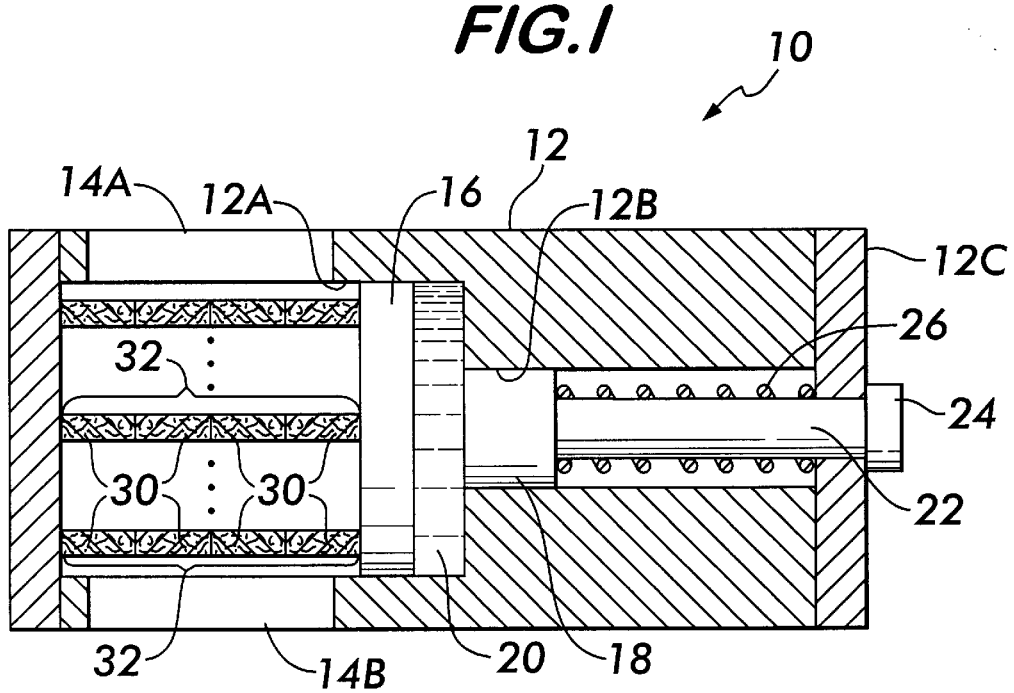
FIG. 1 is a cross-sectional view one embodiment of the water sensor of the present invention prior to its being submerged in water.

Referring now to the drawings, and more particularly to FIG. 1, one embodiment of the present invention water sensor is shown in cross-section and referred to generally by numeral 10. Water sensor 10 has a generally rigid housing 12 that includes one or more ports (e.g., two are illustrated) 14A and 14B formed therein. The interior portion of housing 12 defines a first cylindrical portion 12A and a second cylindrical portion 12B adjacent thereto. First cylindrical portion 12A has a larger diameter than second cylindrical portion 12B. Although portions 12A and 12B are shown coaxially aligned, this need not be the case.

Mounted within first cylindrical portion 12A is a first or drive piston 16 that is configured for sealed but sliding movement within first cylindrical portion 12A. Such sealed fits and movement are well understood in the art of piston/cylinder design and will therefore not be discussed further herein. Mounted within second cylindrical portion 12B is a second or driven piston 18 configured for sealed but sliding movement within second cylindrical portion 12B. Pistons 16 and 18 are spaced apart from one another with the resulting sealed chamber formed therebetween being filled with a hydraulic fluid 20 such as a silicone hydraulic fluid.

A rod 22 is attached to or integral with piston 18. Rod 22 extends from piston 18 through second cylindrical portion 12B and through one end 12C of housing 12. Rod 22 is capped with a head portion 24 that prevents rod 22 from falling into housing 12. Disposed about rod 22 is a spring 26 captured between piston 18 and end 12C of housing 12. Spring 26 is biased to push piston 18 towards piston 16 until head portion 24 seats against end 12C thereby positioning rod 22 substantially in housing 12.

When water sensor 10 is submerged in water, proper operation thereof requires movement of piston 16 towards piston 18. Such movement pressurizes hydraulic fluid 20 which, in turn, drives piston 18 so that rod 22 is pushed further out of housing 12 as spring 26 compresses.

For water sensor 10, movement of piston 16 is brought about by the water-activated expansion of compressed water-absorbent fibers maintained in housing 12. That is, when water sensor 10 is submerged, water enters housing 12 via ports 14A and 14B and comes into contact with the compressed fibers. The water is absorbed by compressed fibers to bring about their expansion. This expansion results in an axial force being applied to piston 16 which, in turn, moves to compress hydraulic fluid 20.

In the illustrated embodiment, the compressed fibers are in the form of pellets 30 of cotton fibers arranged in parallel stacks 32 within a portion of housing 12 that is in communication with ports 14A/14B and piston 16. Each of pellets 30 could be formed from conventional cotton balls which, when pressed under a high load (e.g., 80,000 pounds per square inch), take a set form. Each of pellets 30 is inert in air. However, when pellets 30 are submerged in water, they expand.

Figure 2:
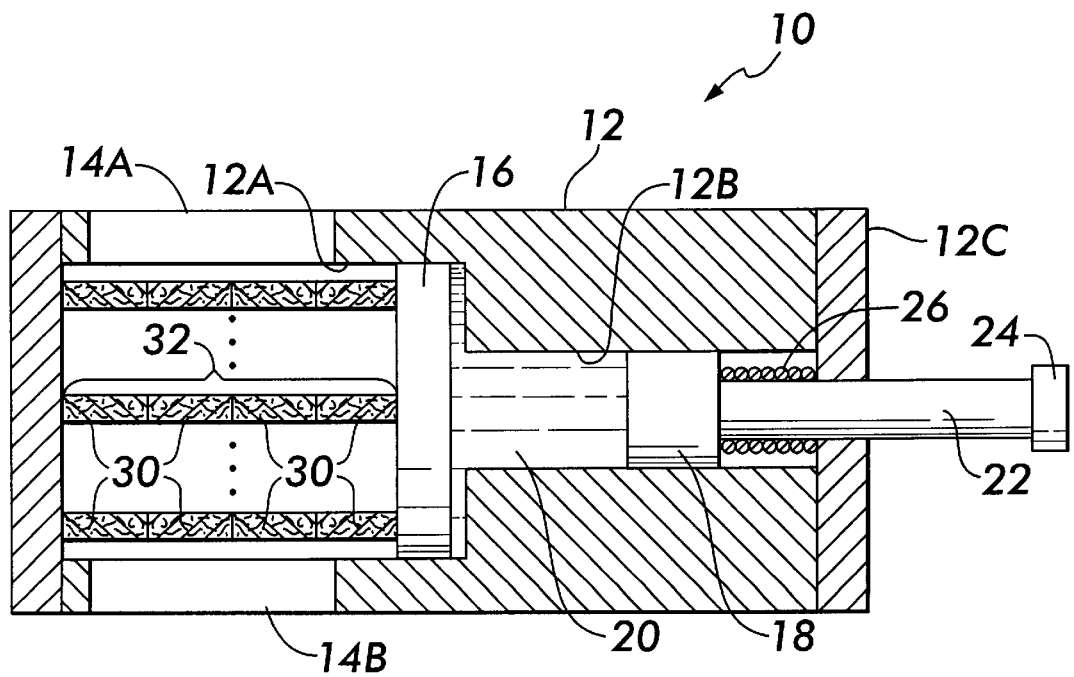
FIG. 2 is a cross-sectional view of the embodiment depicted in FIG. 1 after it has been submerged in water.

When water sensor 10 is submerged in water, ports 14A/14B admit water into housing 12. As they absorb the water, pellets 30 expand in a direction perpendicular to piston 16 as illustrated in FIG. 2. The pellet expansion exerts a force on piston 16 causing it to move towards piston 18 thereby pressurizing hydraulic fluid 20. Once the pressure in hydraulic fluid 20 is sufficient to overcome the spring force of spring 26, piston 18 is driven along second cylindrical portion 12B to force rod 22 further out of housing 12. The extension of rod 22 from housing 12 is thus indicative of the fact that water has entered housing 12.

Figure 3:
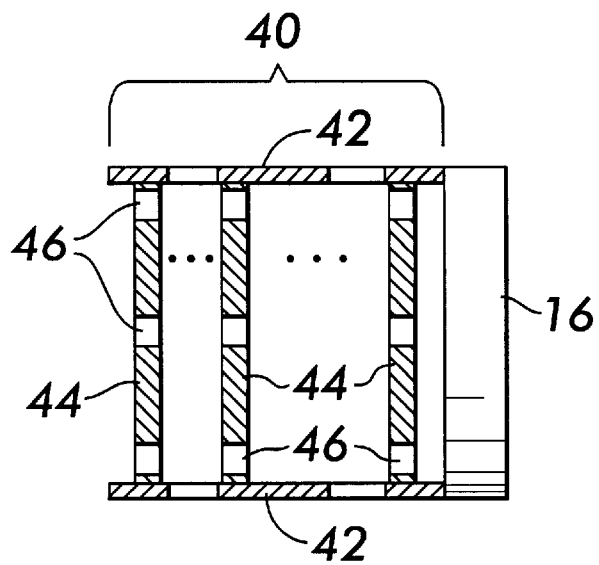
FIG. 3 is an isolated cross-sectional view of the framework used to support the compressed cotton pellets before and after their submergence in water.

In order to constrain the expansion force of pellets 30 perpendicular to the face of piston 16, an open framework supports pellets 30 in housing 12 both before and after their expansion. While a variety of framework designs are possible, one is shown in FIG. 3 and is referenced generally by numeral 40. Note that for clarity of illustration, framework 40 is not shown in FIGS. 1 and 2. Framework 40 includes an exterior cage 42 configured to allow water to pass therethrough. Cage 40 can be, but need not be, attached to or integral with piston 16. Within cage 42 are a plurality of support disks 44 having holes 46 passing therethrough for receiving the cotton pellets, i.e., pellets 30 shown in FIGS. 1 and 2. These cotton pellets slide within holes 46 of disks 44 as they expand.

Figure 4:
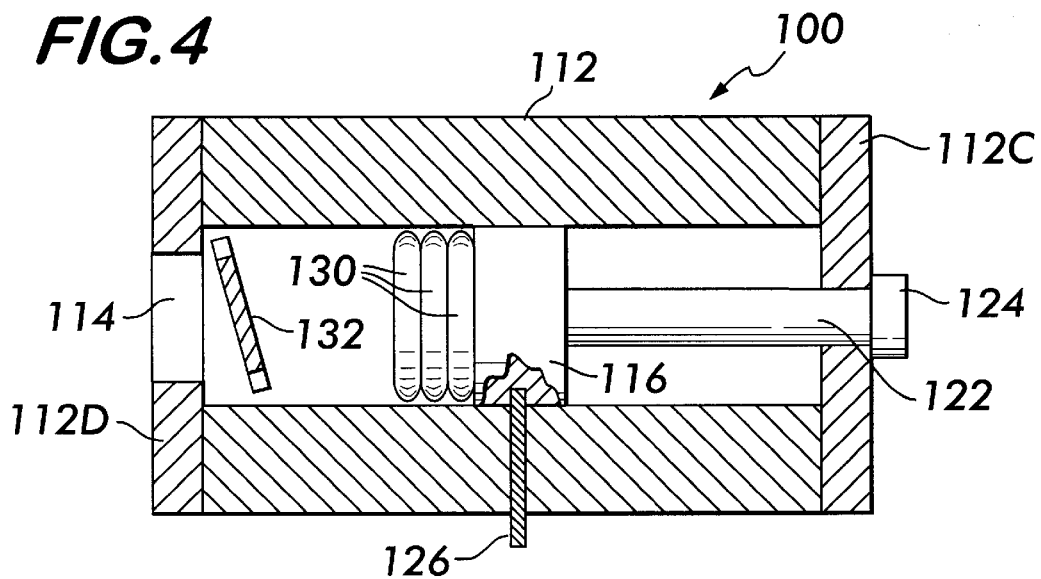
FIG. 4 is a cross-sectional view of another embodiment of the water sensor of the present invention prior to its being submerged in water.
Figure 5:
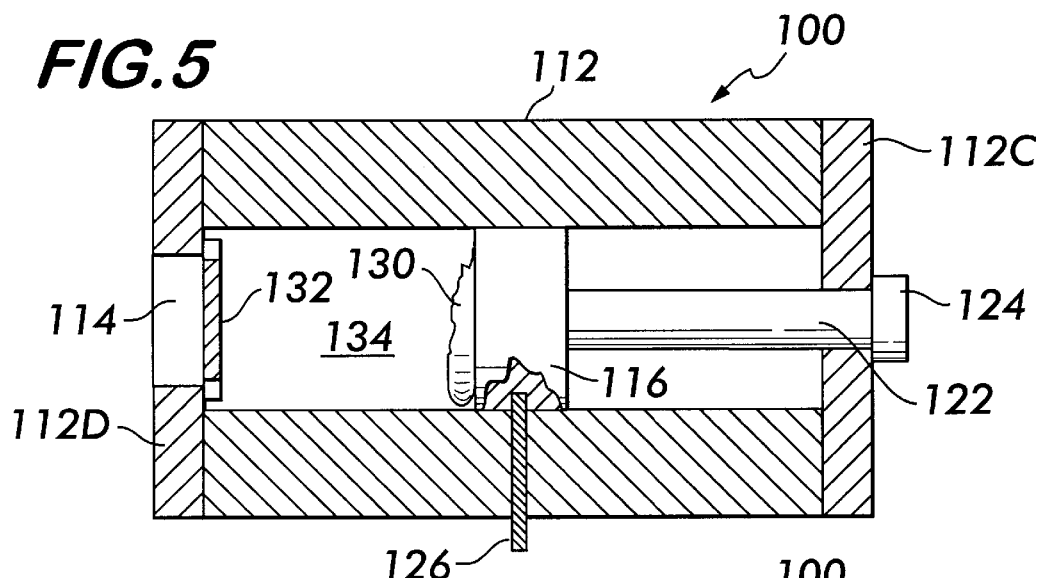
FIG. 5 is a cross-sectional view of the embodiment depicted in FIG. 4 after it has been submerged in water but before the sensor's indicator rod has been extended from the sensor housing.
Figure 6:
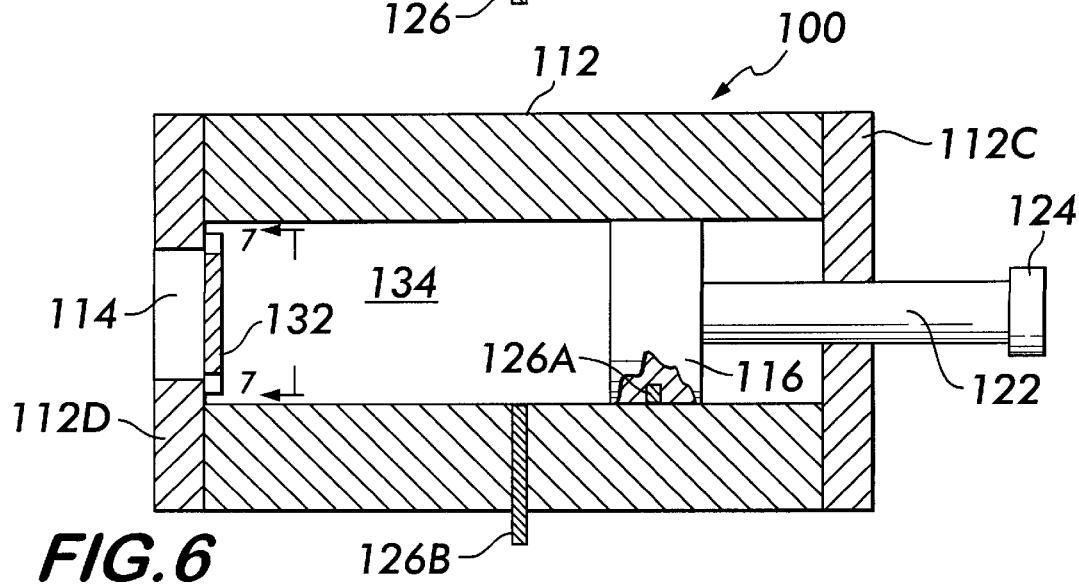
FIG. 6 is a cross-sectional view of the embodiment depicted in FIG. 4 after it has been submerged in water and after the sensor's indicator rod has been extended from the sensor housing.

The second embodiment of the present invention water sensor is illustrated prior to its submergence in water in FIG. 4 and after its submergence in water in FIGS. 5 and 6, and is referenced by numeral 100. Similar to water sensor 10, water sensor 100 has a generally rigid housing 112 with a single port 114 formed therein. Port 114 could also be realized by a plurality of small ports contained within a single area such as that defined by port 114. In this embodiment, the interior portion of housing 112 can define a constant diameter cylinder. Mounted within housing 112 is a drive piston 116 configured for sealed but sliding movement within housing 112. A rod 122 is attached to or integral with piston 116. Rod 122 extends from piston 116 through one end 112C of housing 112. Rod 122 is capped with a head portion 124 that prevents rod 122 from falling into housing 112. To fix the position of piston 116/rod 122, a spring could be used as in water sensor 10. However, other positioners can be used. One such alternative positioner is illustrated in FIG. 4 where the pre-submergence position is maintained by a shear pin coupling one of piston 116 and rod 122 to housing 112. While a variety of shear pin placements are possible, one is shown by way of example in the figures. More specifically, a shear pin 126 passes through housing 112 and into piston 116.

For water sensor 100, movement of piston 116 (to drive rod 122 further from housing 112) is brought about by gas expansion acting on piston 116. In order to prevent such gas expansion from occurring in air while assuring the occurrence of such gas expansion in water, a material that is inert in air but reacts with water to produce gas is used in water sensor 100. The material used is placed in housing 112 such that is in communication with both port 114 and piston 116. In the illustrated embodiment, the material is in the form of tablets 130. The material could also be in the form of pellets, powder, etc. The composition of tablets 130 can be any one of a variety of material compositions that is inert in air but reactive with water to produce gas. Some inexpensive and readily available compositions include pure sodium, calcium carbide and common antacid tablets that are made primarily from citric acid and sodium bicarbonate.

A thin plate or diaphragm 132 is positioned loosely in housing 112 between port 114 and tablets 130. Plate 132 is sized to be larger than port 114. To facilitate the placement of tablets 130 and plate 132, end 112D of housing 112 could be removable. Plate 132 will be used to seal off port 114 as will now be explained.

In operation, water sensor 100 is submerged in water such that water can flow into port 114. The loose placement of plate 132 allows water to flow into housing 112 through port 114. As tablets 130 begin to react with water to produce a gas 134, the gas pressure is initially sufficient to press the loosely disposed plate 132 up against end 112D to seal off port 114 as illustrated in FIG. 5. Sealing of port 114 constrains gas expansion within housing 112. Accordingly, as the reaction between the water and tablets 130 continues, gas expansion exerts pressure on piston 116 until it is sufficient to break shear pin 126 into pieces 126A and 126B as illustrated in FIG. 6. When this occurs, piston 116 moves to drive rod 122 further out of housing 112.

Figure 7:
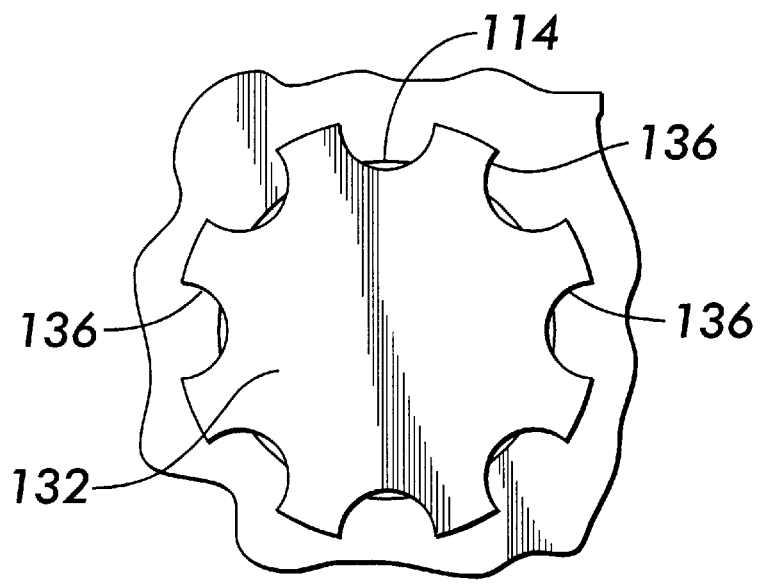
FIG. 7 is a plan view taken along line 7—7 of FIG. 6.

In FIG. 7, a plan view is shown of one embodiment of plate 132 fitted over port 114. Notches 136 can be formed about the periphery of plate 132 and sized so that small amounts of water/gas can pass into/out of port 114 even when plate 132 is over port 114.

The advantages of the present invention are numerous. Each embodiment of the water sensor will positively sense water regardless of the depth thereof. Each cannot be inadvertently activated in air thereby making the design of the present invention a good candidate for use in an underwater explosive device's safety system. Each is of simple mechanical construction and requires no energy of activation other than that made readily available when the sensor is submerged in water.

Although the invention has been described relative to specific embodiments thereof, there are numerous variations and modifications that will be readily apparent to those skilled in the art in light of the above teachings. For example, the housing could be constructed as a unitary body or in sections that are assembled. The hydraulic link used in the expanding fiber embodiment could also be in the expanding gas embodiment. Positioning devices other than a spring (i.e., spring 26 in FIG. 1) and a shear pin (i.e., shear pin 126 in FIG. 4) could be used to set the pre-submergence position of the indicator rod. An indicating means other than a rod could be used. For example, an indicator could be movably mounted in the housing such that movement of the drive piston changed the position of the indicator to indicate that submergence of the sensor had occurred. It is therefore to be understood that, within the scope of the appended claims, the invention may be practiced other than as specifically described.

What is claimed as new and desired to be secured by Letters Patent of the United States is:

1. A water sensor, comprising:

a housing that has at least one inlet port formed therein for allowing water to pass therethrough when said at least one inlet port is submerged in water;

a piston mounted in said housing for sliding engagement therein;

a rod coupled on a first end thereof to a first face of said piston, said rod extending through said housing to a second end of said rod residing outside of said housing;

a positioner for fixing an initial position of said rod relative to said housing before said housing is submerged in water; and an expander in communication with a second face of said piston opposite said first face and in communication with said at least one inlet port, said expander being inert in air and reactive with water to generate a pressure force on said second face which causes said positioner to yield said initial position and said piston to move in said housing, whereby movement of said piston causes said rod to further protrude from said housing.

2. A water sensor as in claim 1 wherein said expander comprises compressed water-absorbent fibers.

3. A water sensor as in claim 2 wherein said water-absorbent fibers are made of cotton.

4. A water sensor as in claim 1 wherein said expander comprises a plurality of pellets of compressed cotton fibers.

5. A water sensor as in claim 4 wherein said plurality of pellets are arranged in a plurality of parallel stacks of pellets.

6. A water sensor as in claim 5 further comprising a framework for supporting said plurality of parallel stacks of pellets.

7. A water sensor as in claim 1 further comprising a hydraulic link for coupling said first face of said piston to said one end of said rod.

8. A water sensor as in claim 1 wherein said positioner comprises a shear pin coupling said rod to said housing.

9. A water sensor as in claim 1 wherein said positioner comprises a spring disposed about said rod within said housing.

10. A water sensor as in claim 1 wherein said expander comprises material that reacts with water to produce gas and wherein said at least one inlet port comprises a single inlet port, said water sensor further comprising a plate loosely disposed in said housing between said material and said single inlet port, said plate being larger than said single inlet port wherein, as said material reacts with water to produce gas, said gas exerts pressure on said plate to cause said plate to seal off said single inlet port, said gas further exerting pressure on said second face of said piston to cause said positioner to yield said initial position and said piston to move in said housing to drive said rod.

11. A water sensor as in claim 10 wherein said material is selected from the group consisting of sodium, calcium carbide and a mixture of citric acid and sodium bicarbonate.

12. A water sensor, comprising:

a housing that has at least one inlet port formed therein for allowing water to pass therethrough when said at least one inlet port is submerged in water;

a drive piston mounted in said housing for sliding engagement therein;

a water-activated driver coupled to said drive piston and in communication with said at least one inlet port, said water-activated driver being inert in air and reactive with water to exert pressure on said drive piston and move said drive piston in said housing; and a movable indicator mounted relative to said housing and responsive to movement of said drive piston, said movable indicator moving from a first position to a second position in response to said movement of said drive piston wherein said second position is indicative of the condition of said at least one inlet port being submerged in water.

13. A water sensor as in claim 12 wherein said water-activated driver comprises compressed water-absorbent fibers.

14. A water sensor as in claim 13 wherein said water-absorbent fibers are made of cotton.

15. A water sensor as in claim 12 wherein said water-activated driver comprises a plurality of pellets of compressed cotton fibers.

16. A water sensor as in claim 15 wherein said plurality of pellets are arranged in a plurality of parallel stacks of pellets.

17. A water sensor as in claim 16 further comprising a framework for supporting said plurality of parallel stacks of pellets.

18. A water sensor as in claim 12 further comprising:

a second piston mounted in said housing for sliding engagement therein, said second piston being spaced apart from said drive piston wherein a sealed chamber is defined between said drive piston and said second piston, said second piston defining a smaller piston surface area than that of said drive piston and said second piston being coupled to said movable indicator; and a hydraulic fluid filling said sealed chamber.

19. A water sensor as in claim 12 wherein said water-activated driver comprises material that reacts with water to produce gas and wherein said at least one inlet port comprises a single inlet port, said water sensor further comprising a plate loosely disposed in said housing between said material and said single inlet port, said plate being larger than said single inlet port wherein, as said material reacts with water to produce gas, said gas exerts pressure on said plate to cause said plate to seal off said single inlet port, said gas further exerting pressure on said drive piston to bring about said movement of said drive piston.

20. A water sensor as in claim 19 wherein said material is selected from the group consisting of sodium, calcium carbide and a mixture of citric acid and sodium bicarbonate.

* * * * *